US008545380B2

(12) United States Patent
Farnan et al.

(10) Patent No.: US 8,545,380 B2
(45) Date of Patent: Oct. 1, 2013

(54) INTRAVASCULAR BLOOD PUMP AND CATHETER

(75) Inventors: Robert C. Farnan, River Vale, NJ (US); Oliver Marseille, Aachen (DE)

(73) Assignee: Circulite, Inc., Teaneck, NJ (US)

( * ) Notice: Subject to any disclaimer, the term of this patent is extended or adjusted under 35 U.S.C. 154(b) by 939 days.

(21) Appl. No.: 12/396,048

(22) Filed: Mar. 2, 2009

(65) Prior Publication Data
US 2009/0171137 A1 Jul. 2, 2009

Related U.S. Application Data (63) Continuation of application No. PCT/US2007/078507, filed on Sep. 14, 2007.

(60) Provisional application No. 60/825,662, filed on Sep. 14, 2006, provisional application No. 60/870,436, filed on Dec. 18, 2006.

(51) Int. Cl.
*A61M 1/12* (2006.01)
(52) U.S. Cl.
USPC .............................................. 600/16; 623/3.1
(58) Field of Classification Search
USPC ............. 600/16–18; 623/3.1, 3.13; 128/898; 604/121, 151, 540
See application file for complete search history.

(56) References Cited

U.S. PATENT DOCUMENTS

| 2,935,068 | A |   | 5/1960  | Donaldson          |
|-----------|---|---|---------|--------------------|
| 3,195,540 | A |   | 7/1965  | Waller             |
| 3,433,227 | A |   | 3/1969  | Kettenbach         |
| 3,903,895 | A |   | 9/1975  | Alley et al.       |
| 3,942,535 | A |   | 3/1976  | Schulman           |
| 4,033,331 | A |   | 7/1977  | Guss et al.        |
| 4,534,761 | A |   | 8/1985  | Raible             |
| 4,790,825 | A |   | 12/1988 | Bernstein et al.   |
| 4,834,724 | A | * | 5/1989  | Geiss et al. ........... 604/540 |
| 4,887,996 | A | * | 12/1989 | Bengmark ............. 604/500 |
| 4,995,857 | A |   | 2/1991  | Arnold             |

(Continued)

FOREIGN PATENT DOCUMENTS

DE 102004019721 A1 10/2005
EP 0364293 A3 3/1991

(Continued)

OTHER PUBLICATIONS

U.S. Patent and Trademark Office, International Preliminary Report on Patentability in PCT Application No. PCT/US08/71938, Apr. 1, 2010.

(Continued)

*Primary Examiner* — Kennedy Schaetzle
*Assistant Examiner* — Erica Lee
(74) *Attorney, Agent, or Firm* — Wood, Herron & Evans, L.L.P.

(57) ABSTRACT

An intravascular system for pumping blood from a chamber of a heart and through an associated blood vessel coupled in fluid communication therewith. The system includes a pump device configured to be inserted into a blood vessel. The system further includes a catheter having a proximal end coupled to the pump device and a distal end configured to collect blood within or exiting from the chamber. The catheter further includes a pre-formed shape corresponding to the vessel to at least assist with stabilization and positioning of the pump device in the vessel.

12 Claims, 5 Drawing Sheets

(56) References Cited

U.S. PATENT DOCUMENTS

| | | | |
|---|---|---|---|
| 5,163,954 | A | 11/1992 | Curcio et al. |
| 5,171,218 | A | 12/1992 | Fonger et al. |
| 5,190,528 | A | 3/1993 | Fonger et al. |
| 5,256,146 | A | 10/1993 | Ensminger et al. |
| 5,287,852 | A | 2/1994 | Arkinstall |
| 5,290,227 | A | 3/1994 | Pasque |
| 5,290,251 | A | 3/1994 | Griffith |
| 5,344,443 | A | 9/1994 | Palma et al. |
| 5,545,191 | A | 8/1996 | Mann et al. |
| 5,695,471 | A | 12/1997 | Wampler |
| 5,697,936 | A | 12/1997 | Shipko et al. |
| 5,704,891 | A | 1/1998 | Mussivand |
| 5,711,753 | A | 1/1998 | Pacella et al. |
| 5,738,649 | A | 4/1998 | Macoviak |
| 5,741,316 | A | 4/1998 | Chen et al. |
| 5,743,845 | A | 4/1998 | Runge |
| 5,840,070 | A | 11/1998 | Wampler |
| 5,843,088 | A | 12/1998 | Barra et al. |
| 5,858,009 | A | 1/1999 | Jonkman |
| 5,921,971 | A | 7/1999 | Agro et al. |
| 5,924,848 | A | 7/1999 | Izraelev |
| 5,924,975 | A | 7/1999 | Goldowsky |
| 5,938,412 | A | 8/1999 | Izraelev |
| 5,941,813 | A | 8/1999 | Sievers et al. |
| 5,947,892 | A | 9/1999 | Benkowski et al. |
| 5,948,006 | A | 9/1999 | Mann |
| 5,965,089 | A | 10/1999 | Jarvik et al. |
| 6,001,056 | A | 12/1999 | Jassawalla et al. |
| 6,017,355 | A | 1/2000 | Hessel et al. |
| 6,116,862 | A | 9/2000 | Rau et al. |
| 6,176,848 | B1 | 1/2001 | Rau et al. |
| 6,186,999 | B1 | 2/2001 | Chen |
| 6,273,861 | B1 | 8/2001 | Bates et al. |
| 6,299,575 | B1 | 10/2001 | Bolling |
| 6,354,299 | B1 | 3/2002 | Fischell et al. |
| 6,358,266 | B1 | 3/2002 | Bonutti |
| 6,406,420 | B1 | 6/2002 | McCarthy et al. |
| 6,530,876 | B1 | 3/2003 | Spence |
| 6,565,536 | B1 | 5/2003 | Sohn |
| 6,605,032 | B2 | 8/2003 | Benkowski et al. |
| 6,623,475 | B1 | 9/2003 | Siess |
| 6,942,611 | B2 | 9/2005 | Siess |
| 6,955,175 | B2 | 10/2005 | Stevens et al. |
| 6,994,666 | B2 | 2/2006 | Shannon et al. |
| 7,048,681 | B2 | 5/2006 | Tsubouchi et al. |
| 7,070,555 | B2 | 7/2006 | Siess |
| 7,077,801 | B2 | 7/2006 | Haverich |
| 7,340,288 | B1 | 3/2008 | Karicherla et al. |
| 2003/0093104 | A1 | 5/2003 | Bonner et al. |
| 2003/0187322 | A1 | 10/2003 | Siess |
| 2004/0015150 | A1 | 1/2004 | Zadno-Azizi |
| 2004/0024285 | A1 | 2/2004 | Muckter |
| 2004/0024435 | A1 | 2/2004 | Leckrone et al. |
| 2004/0193004 | A1 | 9/2004 | Tsubouchi et al. |
| 2004/0236170 | A1 | 11/2004 | Kim |
| 2005/0107658 | A1 | 5/2005 | Brockway |
| 2005/0159711 | A1 | 7/2005 | Kathrani et al. |
| 2006/0094983 | A1 | 5/2006 | Burbank et al. |
| 2006/0100565 | A1 | 5/2006 | Aboul-Hosn |
| 2006/0116746 | A1 | 6/2006 | Chin |
| 2006/0135946 | A1 | 6/2006 | Moehle et al. |
| 2006/0235357 | A1 | 10/2006 | Woodward et al. |

FOREIGN PATENT DOCUMENTS

| | | |
|---|---|---|
| EP | 0963764 A1 | 12/1999 |
| EP | 1013301 B1 | 11/2004 |
| JP | 2203867 A | 8/1990 |
| JP | 10272187 A | 10/1998 |
| JP | 2000185102 A | 7/2000 |
| JP | 2004506490 A | 3/2004 |
| JP | 2004514506 A | 5/2004 |
| WO | 9742413 A1 | 11/1997 |
| WO | 9959652 A1 | 11/1999 |
| WO | 0180927 A2 | 11/2001 |
| WO | 2004/091716 A1 | 10/2004 |
| WO | 2008/034068 A2 | 3/2008 |

OTHER PUBLICATIONS

U.S. Patent and Trademark Office, International Preliminary Report on Patentability in PCT Serial No. PCT/US08/081082, Apr. 26, 2010.

U.S. Patent and Trademark Office, Office Action in U.S. Appl. No. 11/846,839, Apr. 29, 2010.

R. J. Baird, M.D. et al., Survey of Mechanical Assistance of the Circulation and the Present Status of Left-Heart Bypass, Article, pp. 340-345, 1965.

R. J. Baird F.R.C.S.(C) et al., Le Support Mechanique Du Ventricule Gauche, Article, pp. 258-268, Dec. 1964.

World Heart Corporation, World Heart, 1998 Annual Report, 36 pgs.

U.S. Patent and Trademark Office, International Search Report and Written Opinion in PCT Application Serial No. PCT/US07/61118, Nov. 2, 2007.

U.S. Patent and Trademark Office, International Search Report and Written Opinion in PCT Application Serial No. PCT/US07/78507, Mar. 14, 2008.

U.S. Patent and Trademark Office, International Search Report and Written Opinion in PCT Application Serial No. PCT/US07/76956, Aug. 19, 2008.

U.S. Patent and Trademark Office, International Search Report and Written Opinion in PCT Application Serial No. PCT/US07/66046, Oct. 8, 2008.

U.S. Patent and Trademark Office, International Search Report and Written Opinion in PCT Application Serial No. PCT/US08/71938, Nov. 3, 2008.

U.S. Patent and Trademark Office, International Search Report and Written Opinion in PCT Application Serial No. PCT/US08/71922, Nov. 3, 2008.

O.H. Frazier, MD et al., The HeartMate® Left Ventricular Assist System, Texas Heart Institute Journal, vol. 25, No. 4, 1998, pp. 265-271.

J. Mark Burnett, RCP et al., Intracardiac Echocardiography 101: The Beginner's Guide to ICE Imaging and Cardiac Structure Recognition, http://www.eplabdigest.com/article/4148, Dec. 13, 2007.

U.S. Patent and Trademark Office, International Preliminary Examination Report in PCT Application No. PCT/US07/76956, Feb. 4, 2009.

U.S. Patent and Trademark Office International Search Report and Written Opinion in PCT Application No. PCT/US2008/081082, Feb. 10, 2009.

Japanese Patent Office, Decision on Rejection in JP Application No. 2009-528501, Jan. 15, 2013 (including English Translation).

Japanese Patent Office, Notice of Reasons for Rejection in JP Application No. 2009-528501, Jul. 24, 2012 (including English Translation).

* cited by examiner

FIG. 8

INTRAVASCULAR BLOOD PUMP AND CATHETER

This application is a continuation of PCT Application Ser. No. PCT/US2007/078507, filed Sep. 14, 2007 (pending) which claims the priority benefit of U.S. Provisional Patent Application Ser. No. 60/825,662, filed Sep. 14, 2006 (expired) and U.S. Provisional Patent Application Ser. No. 60/870,436, filed Dec. 18, 2006 (expired), the disclosures of which are incorporated by reference herein in their entirety.

TECHNICAL FIELD

The present disclosure relates to vascular blood pump systems, and more specifically, to an intravascular blood pump system for pumping blood through an artery.

BACKGROUND

Intravascular blood pumps are a class of blood pumps or circulatory assist devices that may be implanted into the vascular system (e.g., the veins or arteries) of a patient in either a percutaneous manner or a surgical manner. They may be used to assist the volume of blood being ejected from the left or right side of the heart. A particular intravascular pump is known generally as an axial flow blood pump and includes a rotor or impeller surrounded by a protective housing. These components (i.e., the pump, the rotor and housing) and any other components connected therewith are coupled to the distal end of a flexible catheter. The catheter may be inserted into the vascular system, such as through generally remote access into a femoral artery. The catheter may ultimately be directed to and finally positioned in the ascending aorta proximate to the left side of the heart, as one example. Rotational force on one or more impeller blades associated with the implanted pump may be imparted by way of a mechanical connection and drive or, for example, a magnetic connection and drive.

Despite the advances made in this area of blood pumps and systems, it remains desirable to provide improvements, for example, related generally to guiding, positioning, stabilizing and operating intravascular blood pumps and systems incorporating such blood pumps.

SUMMARY

In an illustrative embodiment, an intravascular system for pumping blood from a chamber of a heart and through an associated blood vessel coupled in fluid communication therewith is provided. The system includes a pump device configured to be inserted into a blood vessel. The system further includes a catheter having a proximal end coupled to the pump device and a distal end configured to collect blood within or exiting from the chamber. The catheter further includes a pre-formed shape corresponding to the vessel to at least assist with stabilization and positioning of the pump device in the vessel.

The catheter used in any of the embodiments encompassed herein may further include first and second lumens. The first lumen is configured to transport blood from the distal end to the proximal end and the system may further include a wire inserted into the second lumen and configured to define the pre-formed shape of the catheter. The catheter may further include a helical portion, with the helical portion being configured to facilitate securing the first end in the vessel. At least a portion of the catheter may extend along an axis and the helical portion may then extend around the axis generally parallel to a plane transverse to the axis. The catheter may further comprise a lumen extending from the distal end to the proximal end and at least one inlet aperture into the lumen on the helical portion. The at least one inlet aperture may be positioned generally to face the axis to minimize suction with vascular walls.

Also in the various embodiments, the catheter may further include radiopaque markers to facilitate positioning the catheter and the pump device within the vascular system.

A lumen in the catheter may extend from the distal end to the proximal end with a guidewire entry port communicating with the lumen at the distal end, and a guidewire exit port communicating with the lumen at the proximal end.

A pump device is provided and is usable in connection with any embodiment encompassed herein. The pump device includes a pump housing having a first end coupled to the catheter and a tubular body extending from the first end along an axis. The tubular body includes an outer surface and at least one side outlet port extending through the outer surface. A pump is positioned within the tubular body of the pump housing. A motor housing is also coupled to the pump housing, and a motor is positioned within the motor housing. The motor is configured to operate the pump so that blood is drawn from the catheter, through the pump housing, and exits from the at least one side port.

In another embodiment, an intravascular pump device for pumping blood from a catheter is provided and includes a pump housing having a first end adapted to be coupled to the catheter, a second end, and a tubular body extending between the first and second ends along an axis. A pump is positioned within the tubular body of the pump housing. A motor housing is coupled to the pump housing along the axis and is positioned proximate the second end. The motor housing has a diameter smaller than the tubular body such that the pump housing defines an outlet extending along the axis between the tubular body and the motor housing. A motor is positioned within the motor housing with the motor being configured to operate the pump so that blood is drawn from the catheter, moves through the tubular body of the pump housing, and exits from the outlet.

With regard to the pump devices usable in connection with the other components encompassed herein, a power cable may be coupled to the motor housing along the axis or lengthwise direction of the tubular body. The motor housing may include a tapered portion, for example, generally along the axis or lengthwise direction. The pump housing may be defined by a pump inlet housing coupled to the catheter and a pump outlet housing coupled to the motor housing. The pump outlet housing may further include at least two vanes coupling the motor housing to the pump outlet housing.

Various additional features and aspects of the embodiments and scope of the invention will be more readily appreciated upon review of the following detailed description of the illustrative embodiments taken in conjunction with the accompanying drawings.

DETAILED DESCRIPTION

Figure 1:
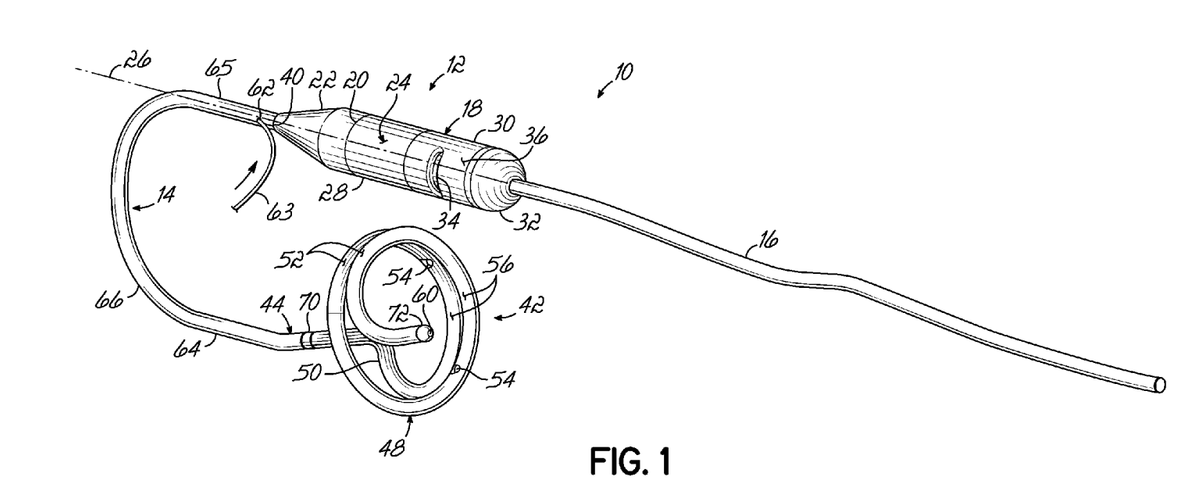
FIG. 1 is a perspective view of one embodiment of a blood pump system.

With reference to FIG. 1, one embodiment of an intravascular blood pump system 10 is shown. The system generally includes a pump device 12, a catheter 14, and a pump cable 16 for supplying electrical power to the pump device 12. The system 10 is configured to be inserted into a blood vessel, such as a vein or artery, to pump blood from within a chamber of the heart or at least a location close to an exit of a chamber, and then through the associated vessel, as will be described in greater detail below.

Figure 2:
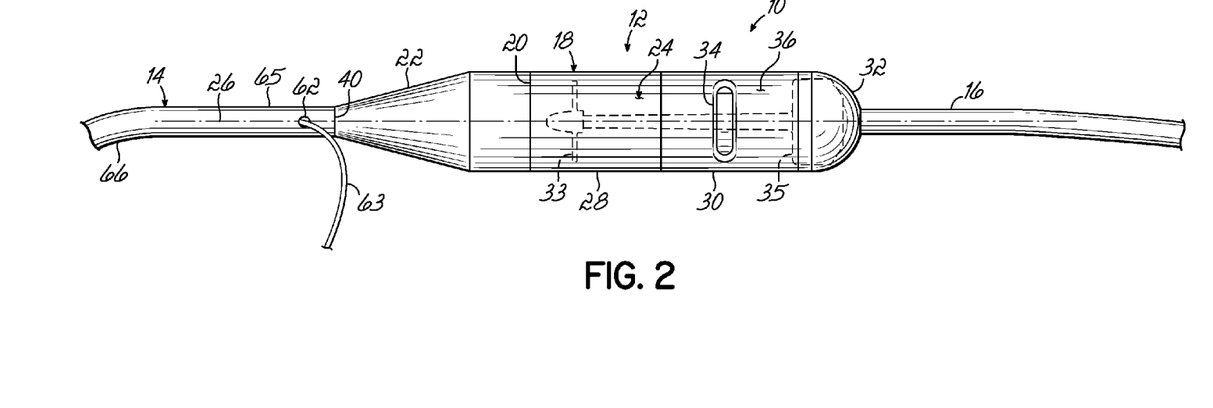
FIG. 2 is a front elevational view of a pump device of the blood pump system shown in FIG. 1.
Figure 9:
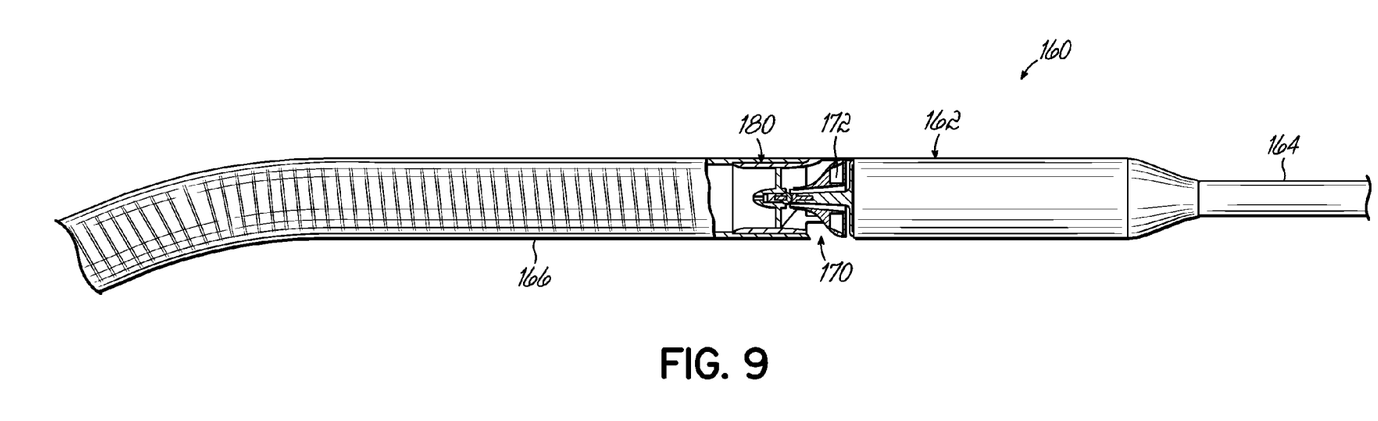
FIG. 9 is an enlarged view of the blood pump system shown in FIG. 8 and partially fragmented to show internal portions of the inflow housing.
Figure 10:
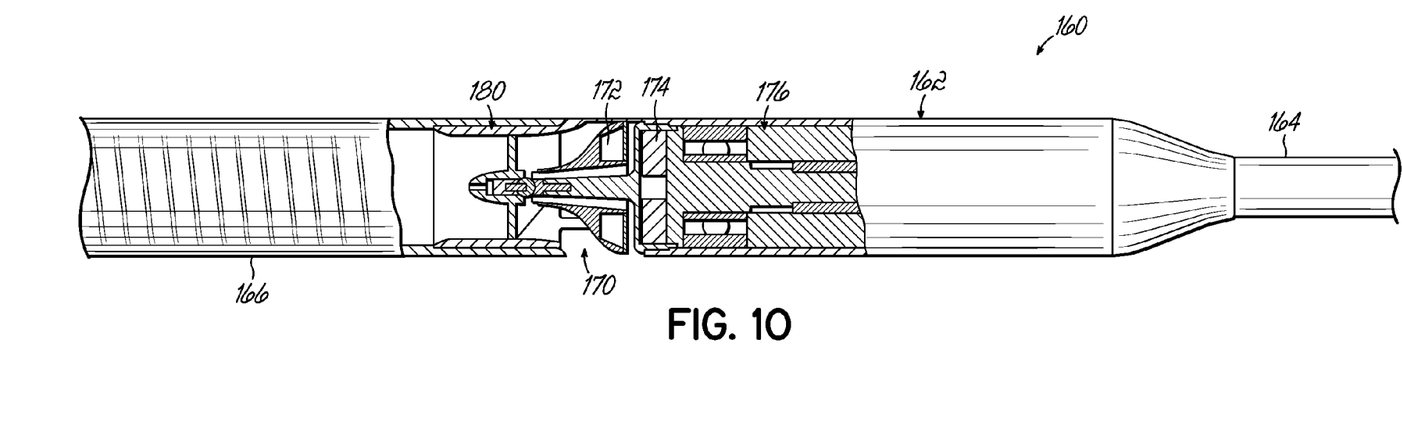
FIG. 10 is a further enlarged view of the blood pump and inflow sections shown in FIG. 9 and partially fragmented to show internal structure of the inflow housing and blood pump.

As shown in FIGS. 1 and 2, the pump device 12 includes an elongate pump housing 18 having a first end 20 coupled to a transition portion 22 of the catheter 14 and tubular body 24 extending from the first end 20 along a longitudinal axis 26 of the pump housing 18. The first end 20 may be secured to the transition portion 22 by rigid barbs, adhesive, or any other coupling technique. In one embodiment, the tubular body 24 is defined by a pump inlet housing 28 and a pump outlet housing 30. The pump inlet housing 28 and pump outlet housing 30 may secured together by internal threads, adhesive, laser welding, or any other suitable coupling technique. Various components of a blood pump are housed within the pump housing 18 to draw blood from the catheter 14 into the tubular body 24. For example, the blood pump may comprise an impeller 33 and associated impeller blades positioned within the pump inlet housing 28. A motor 35 positioned within a motor housing 32 proximate the pump outlet housing 30 rotates the impeller 33 to draw blood through the tubular body 24. It will be appreciated that the impeller 33 and motor 35 are only schematically illustrated and may take many forms, including a form as generally shown in FIGS. 9 and 10 herein.

The motor housing 32 may be sealingly coupled to the pump outlet housing 30 and the transition portion 22 may be sealingly coupled to the pump inlet housing 28 to help control the flow of blood within the tubular body 24. One or more side outlet ports, slots, or apertures 34 extend through an outer surface 36 of the pump outlet housing 30 so that the blood drawn into the tubular body 24 through the catheter 14 by the blood pump may be delivered to the blood vessel, such as the vein or artery, into which the system 10 has been inserted. To eliminate sharp edges and to prevent areas of stagnant blood flow, the motor housing 32 may be designed with a dome-shaped configuration as shown. The motor housing 32 may also be configured to couple to the pump cable 16 along the longitudinal axis 26. Such an arrangement further reduces the amount of stagnation so as to minimize the formation of thrombus.

Figure 3:
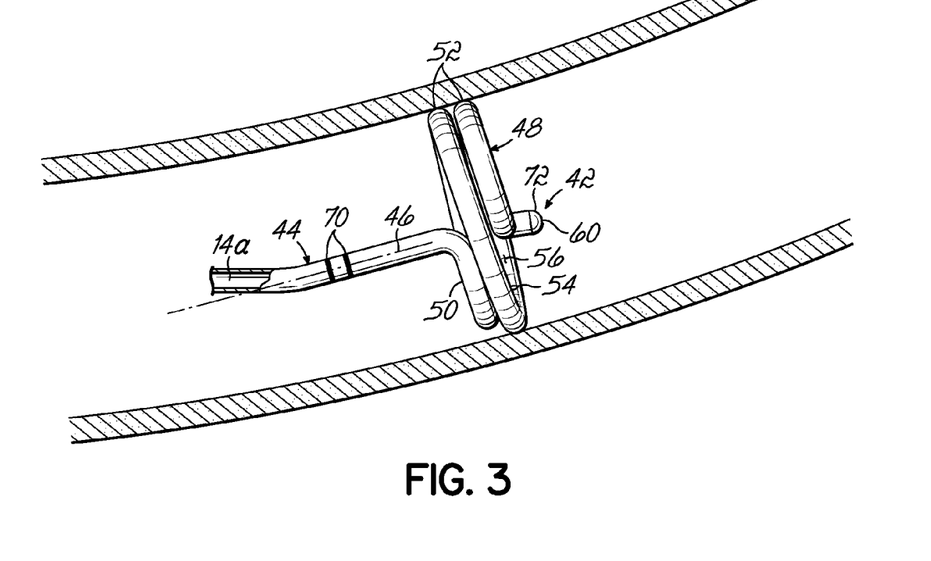
FIG. 3 is a front elevational view of a portion of a catheter used in the blood pump system of FIG. 1.
Figure 4:
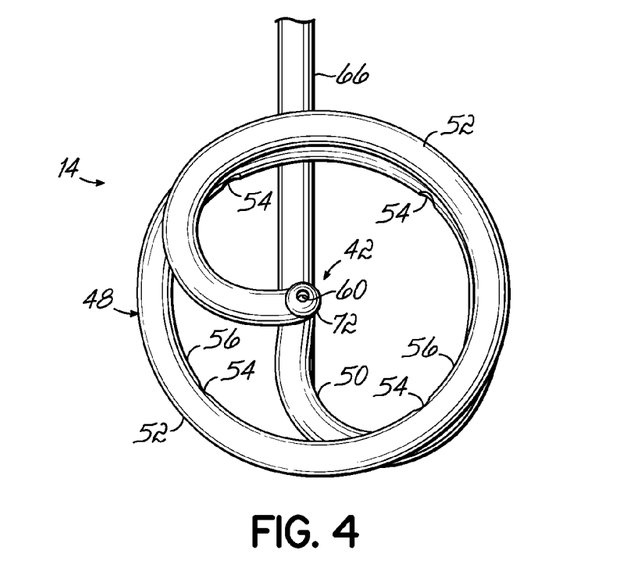
FIG. 4 is a side elevational view of a portion of the catheter shown in FIG. 4.

Referring to FIGS. 1, 3, and 4, the catheter 14 includes a proximal end 40 (FIG. 1) coupled to the transition section 22, a distal end 42 configured to collect blood exiting from a heart chamber, such as a ventricle, and a lumen 14a extending between the proximal and distal ends 40, 42 within the catheter 14. More specifically, the distal end 42 has a substantially linear portion 44 extending along an axis 46 and a substantially helical portion 48 extending around the axis 46. The helical portion 48 first extends transverse to the axis 46 before wrapping around it in a helical configuration generally parallel to a plane that is transverse to the axis 46. For example, the helical portion 48 may include a transverse section 50 extending from the substantially linear portion 44 in a plane substantially perpendicular to the axis 46. The length of the transverse section 50 may vary depending upon the desired diameter of the helix formed by the helical portion 48. The diameter of the helix is preferably large enough so that outer surfaces 52 of the helical portion 48 contact or interact with the walls of the blood vessel into which the catheter 14 is inserted. Such an arrangement secures the catheter 14 within the blood vessel so that it is stabilized and may not be easily retracted. The catheter 14 may be pre-formed formed with the desired shape so that the helical portion 48 retains its helical configuration after the catheter's insertion, as will be described below.

The helical portion 48 defines at least half of a full helix and may have a pitch greater than or equal to the outer diameter of the catheter 14. Inlet apertures 54 positioned on inner surfaces 56 of the helical portion 48 communicate with the lumen 14a of the catheter 14. The inlet apertures 54 may be circular, elliptical, triangular, or any other shape, and their cross-sectional areas may be greater than the cross-sectional area of the catheter lumen 14a. The greater cross-sectional area allows blood to be freely drawn into and through the lumen 14a when the pump device 12 is activated. This prevents blood stagnation and the formation of thrombus outside of the lumen 14a. Also, by virtue of the inlet apertures 54 being positioned on the inner walls 56 and generally facing toward the axis 46, the catheter 14 avoids a "suction effect" with adjacent vascular walls and structures when the pump device 12 is activated. In other words, the inlet apertures 54 should not engage the vessel wall.

The catheter 14 and pump device 12 may be inserted into the blood vessel in a variety of ways. For example, in one embodiment the catheter 14 includes a guidewire entry port 60 on a distal tip 72 and a guidewire exit port 62 proximate the transition section 22. After inserting a guidewire 63 into the blood vessel, the catheter 14 may be advanced over the guidewire 63 until it is properly positioned. The guidewire 63 may then be removed by retracting it through the guidewire exit port 62. In an alternative embodiment, the catheter 14 may be inserted into the blood vessel through a sheath (not shown) and thus would not require the guidewire entry and exit ports 60, 62. A hydrophilic coating may be applied to the catheters disclosed herein to facilitate insertion. Additionally, an anti-thromotic coating may also be applied to the catheters to minimize the formation of thrombus.

The catheter 14 may be made from a variety of materials, including but not limited to, silicone and polyurethane. The catheter 14 may also be comprised of a composite construction that incorporates a wire braid or coil. As mentioned above, the catheter 14 may be pre-formed with a helix or other shape so that the helical portion 48 retains its shape after insertion. In other words, after the catheter 14 is manipulated and advanced into the blood vessel in an expanded, non-helical form, or straightened form, using a guidewire, sheath, or other insertion technique, the helical portion 48 can return to its pre-formed helical shape upon removal of the guidewire, sheath, or other restraint. In one embodiment, the catheter 14 is pre-formed with a helical configuration using standard heat forming techniques. In another embodiment, the catheter 14 incorporates a pre-formed NiTi or other shape memory wire or material (not shown) for defining the helical shape. The wire may be located in a separate, dedicated lumen or otherwise incorporated into the catheter 14. Thus, in such an embodiment the catheter 14 has two lumens—one for delivering blood to the pump device and one for receiving the NiTi wire.

The system 10 may be delivered to the vascular system using endovascular techniques and may be designed to assist a particular heart chamber. For example, when designed to assist the right ventricle, the blood pump device 12 may be subcutaneously inserted into the vena cava with the catheter 14 extending toward the tricuspid valve. When designed to assist the left ventricle, the blood pump device 12 may be subcutaneously inserted into the descending aorta with the catheter 14 extending toward the aortic valve. The pump device 12 may therefore be sized to be received in a blood vessel of the vascular system. In one embodiment, the pump housing 18 has an outer diameter of approximately 13 mm.

Properly positioning the system 10 within the vascular system can be a significant challenge due to bends and convolutions of the various blood vessels. To address these challenges, the catheter 14 may be constructed with a combination of appropriately sized straight sections 44, 64, 65 and curved sections 66. For example, the curved section 66 may be designed to reflect the curvature of the aortic arch if the system is used to assist the left ventricle. Additionally, the length of the section 65 at the proximal end 40 may be selected to be a short distance to position the pump device 12 immediately proximate the curved section 66 within the blood vessel (such as the aorta with the curved section 66 corresponding to a location near the aortic arch) or a longer distance to position the pump device 12 proximate the endovascular entry site (typically the femoral artery) above bifurcation in the iliac artery. The shapes of the various catheter sections 44, 64, 65, 66 are similar to those of guiding catheters used for coronary access. The catheter sections may also be pre-formed to desired shapes using the same techniques discussed above with respect to the helical portion 48.

To further assist positioning within the vascular system, the catheter 14 may include one or more radiopaque bands 70 at desired locations along the catheter 14. FIGS. 1 and 3 illustrate two radiopaque bands 70 on the substantially linear portion 44 of the distal end 42. The distal end 42 may also be provided with a radiopaque tip 72 to further facilitate positioning the system relative to an anatomical landmark such as the aortic or tricuspid valve.

Figure 5:
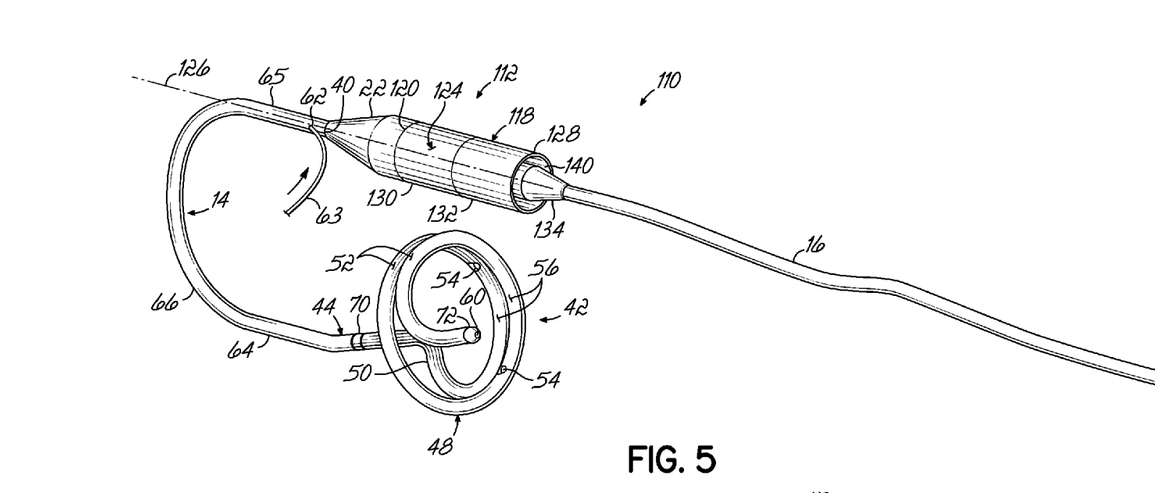
FIG. 5 is a perspective view of another embodiment of a blood pump system.
Figure 6:
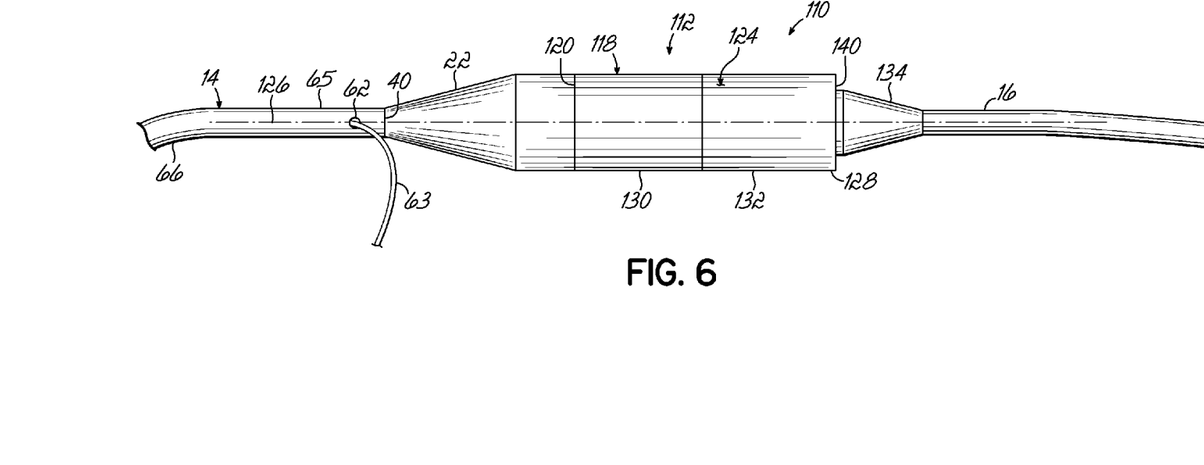
FIG. 6 is a front elevational view of a pump device of the blood pump system shown in FIG. 5.
Figure 7:
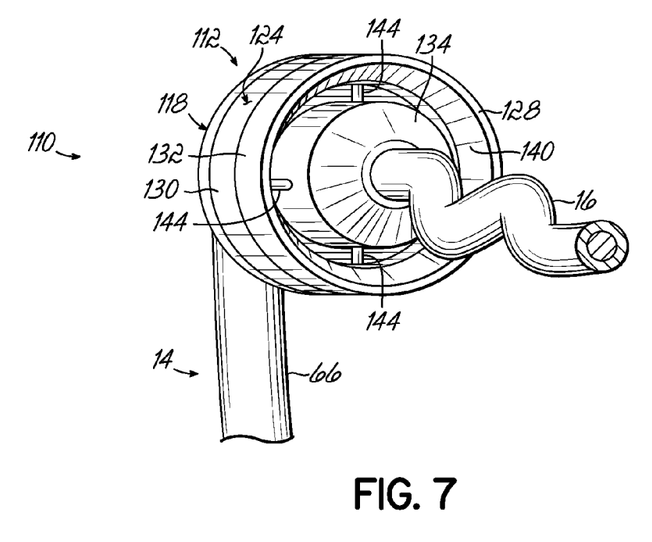
FIG. 7 is a perspective view showing an outlet end of the pump device shown in FIG. 6.

Now referring to FIGS. 5-7, an intravascular blood pump system 110 according to a second embodiment is shown. The system 110 includes the same catheter 14 and pump cable 16 as the system 10. Because reference can be made to the description of these components in FIGS. 1-4, only the differences between the systems 10 and 110 will be described in detail.

Figure 8:
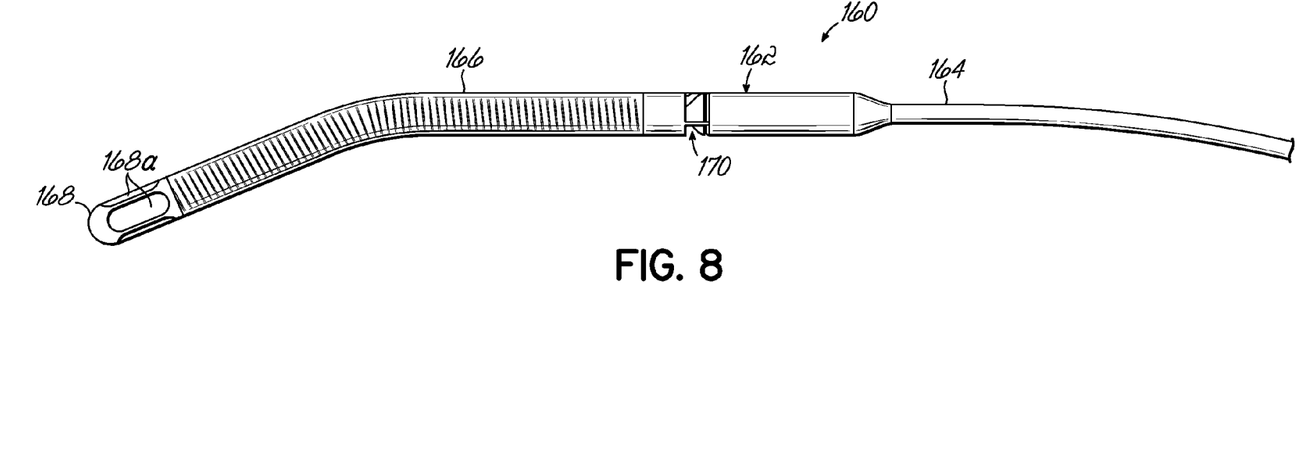
FIG. 8 is an elevational view of another embodiment of a blood pump system.

The system 110 includes a pump device 112 having an elongate pump housing 118 with a first end 120 coupled to the transition section 22 of the catheter 14. A tubular body 124 extends from the first end 120 along an axis 126 and terminates at a second end 128. In one embodiment, a pump inlet housing 130 and a pump outlet housing 132 define the tubular body 124. The tubular body 124 houses the various components of a pump, such as shown in FIGS. 8-10 and described further below. A motor (not shown) positioned within a motor housing 134 drives the components of the pump to draw blood into and through the tubular body 124.

Instead of incorporating side ports for blood to exit the pump device 112, the pump housing 118 defines an opening or outlet 140 at the second end 128. Although the motor housing 134 is positioned proximate the second end 128, the motor housing 134 has a smaller diameter than the outlet 140 so that the impeller blades may pump blood out of the pump device 12 and into the blood vessel. The motor housing 134 may be designed with a tapered portion as shown to prevent abrupt changes in blood flow and minimize areas of stagnation. This coaxial arrangement of the pump and outlet 140 allows the pump device 112 to be positioned adjacent the wall of the blood vessel without imposing a direct fluid force against the wall.

As shown in FIG. 7, the motor housing 134 may be coupled to the pump housing 118 by vanes 144. The device 112 preferably incorporates at least two vanes 144 to secure the motor housing 134 during operation. The vanes 144 have contours designed to minimize their disruption of the blood flow through the tubular body 124. Additionally, radii are provided where the vanes 144 couple to the motor housing 134 and pump housing 118 to minimize thrombus formation and any potential damage to the blood flowing through the tubular body.

FIGS. 8-10 illustrate a blood pump system 160 according to a third embodiment. The system 160 includes a pump device 162 receiving power from a suitable cable 164 in the form of a catheter device that may be inserted through the vascular system of the patient. The pump 162 is connected to a distal catheter portion 166 having a blood inflow tip 168. Catheter portion 166 may have a preformed, angled shape as shown. The blood inflow tip 168 includes suitable openings 168a for allowing blood to be drawn into the tip portion 166. A blood outflow or exit 170 is provided adjacent to the pump 162. Referring more specifically to FIGS. 9 and 10, the blood outflow comprises openings 170 adjacent to a pump rotor 172 that is magnetically coupled to the rotating output 174 of the pump motor 176. The pump motor 176 is therefore completely sealed and respective permanent magnets carried on the pump rotor 172 and the rotating output 174 transfer rotation from the output 174 to the rotor 172 which is supported for rotation in the inflow housing 180. In one suitable use of system 160, the intravascular pump 162 may reside in a patient's aorta, with tip portion 166 extending through the aortic valve such that the inflow tip 168 resides within the left ventricle of the patient. Blood would therefore be drawn from the ventricle into the inflow tip 168 through openings 168a, then travel through tip portion 166 and exit at the outflow openings 170 into the patient's aorta. This would assist with expelling blood from the patient's left ventricle.

While the present invention has been illustrated by a description of various illustrative embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. An intravascular system for pumping blood from a chamber of a heart and through a blood vessel, comprising:
   a pump device configured to be inserted into a blood vessel; and a catheter having a proximal end coupled to said pump device, a distal end configured to collect blood, and a first lumen extending from said distal end to said proximal end for transporting blood collected through the distal end, said catheter extending along an axis;

said catheter including a helical portion proximate said distal end, said helical portion being pre formed in shape to conform to adjacent tissue and at least assist with stabilizing and positioning the pump device in the blood vessel, said helical portion extending around said axis generally parallel to a plane transverse to said axis and including an inner portion facing toward said axis and an outer portion facing away from said axis;

wherein said outer portion further comprises a continuous, solid wall and said inner portion further comprises at least one inlet aperture into said first lumen of said helical portion, said at least one inlet aperture being positioned to generally face said axis.

2. The system of claim 1, wherein said catheter further includes a second lumen, the system further comprising:
a wire inserted into said second lumen, said wire configured to define the shape of the helical portion of said catheter.

3. The system of claim 1, wherein said catheter further includes one or more radiopaque markers to facilitate positioning said catheter and said pump device within a vascular system.

4. The system of claim 1, wherein said catheter further comprises a guidewire entry port in said distal end and a guidewire exit port in said proximal end, said entry and exit ports communicating with said first lumen.

5. The system of claim 1, wherein said pump device comprises:
a pump housing having a first end coupled to said catheter and a tubular body extending from said first end along an axis, said tubular body having an outer surface and at least one side outlet port extending through said outer surface;
a pump positioned within said tubular body of said pump housing;
a motor housing coupled to said pump housing; and
a motor positioned within said motor housing, said motor being configured to operate said pump so that blood is drawn from said catheter, through said pump housing, and exits from said at least one side outlet port.

6. The system of claim 5, wherein said motor housing has a dome-shaped portion extending along said axis, said dome-shaped portion being configured to prevent areas of stagnant blood flow.

7. The system of claim 5, further comprising:
a power cable coupled to said motor housing along said axis.

8. The system of claim 1, wherein said pump device comprises:
a pump housing; and
a motor housing coupled to said pump housing;
wherein said pump housing is defined by a pump inlet housing coupled to said catheter and a pump outlet housing coupled to said motor housing.

9. The system of claim 8, wherein said pump outlet housing further includes at least two vanes coupling said motor housing to said pump outlet housing.

10. The system of claim 1, wherein said pump device comprises:
a pump housing having a first end coupled to said catheter and a tubular body extending from said first end along an axis;
a pump positioned within said tubular body of said pump housing; and
a motor housing coupled to said pump housing, wherein said motor housing has a first diameter and said tubular body has a second diameter, the first diameter being smaller than the second diameter such that said pump housing defines an outlet extending along said axis between said tubular body and said motor housing; and
a motor positioned within said motor housing, said motor being configured to operate said pump so that blood is drawn from said catheter, through said pump housing, and exits from said outlet.

11. The system of claim 10, further comprising:
a power cable coupled to said motor housing along said axis.

12. The system of claim 10, wherein said motor housing has a tapered portion extending along said axis, said tapered portion being configured to prevent areas of stagnant blood flow.

* * * * *